US00PP25453P3

(12) United States Plant Patent
MacGregor

(10) Patent No.: US PP25,453 P3
(45) Date of Patent: Apr. 21, 2015

(54) APPLE TREE NAMED 'MAC 2137'

(50) Latin Name: ***Malus domestica* Mill**
Varietal Denomination: MAC 2137

(71) Applicant: David W. MacGregor, South Haven, MN (US)

(72) Inventor: David W. MacGregor, South Haven, MN (US)

( * ) Notice: Subject to any disclaimer, the term of this patent is extended or adjusted under 35 U.S.C. 154(b) by 196 days.

(21) Appl. No.: 13/694,288

(22) Filed: Nov. 14, 2012

(65) Prior Publication Data

US 2013/0333079 P1 Dec. 12, 2013

Related U.S. Application Data

(60) Provisional application No. 61/629,302, filed on Nov. 15, 2011.

(51) Int. Cl.
*A01H 5/00* (2006.01)

(52) U.S. Cl.
USPC ..... Plt./161

(58) Field of Classification Search
CPC ..... A01H 5/08
USPC ..... Plt./161
See application file for complete search history.

*Primary Examiner* — Kent L Bell
(74) *Attorney, Agent, or Firm* — Michelle Bos

(57) ABSTRACT

A new and distinct apple tree named 'MAC 2137' is disclosed. The new apple is notable for its attractive appearance, superb texture, improved flavor and early ripening.

2 Drawing Sheets

Latin name of the genus and species of the plant claimed: *Malus domestica* Mill.

Variety denomination: 'MAC 2137'.

STATEMENT REGARDING FEDERALLY SPONSORED RESEARCH OR DEVELOPMENT

None

BRIEF DESCRIPTION OF THE PHOTOGRAPHS

Figure 1:
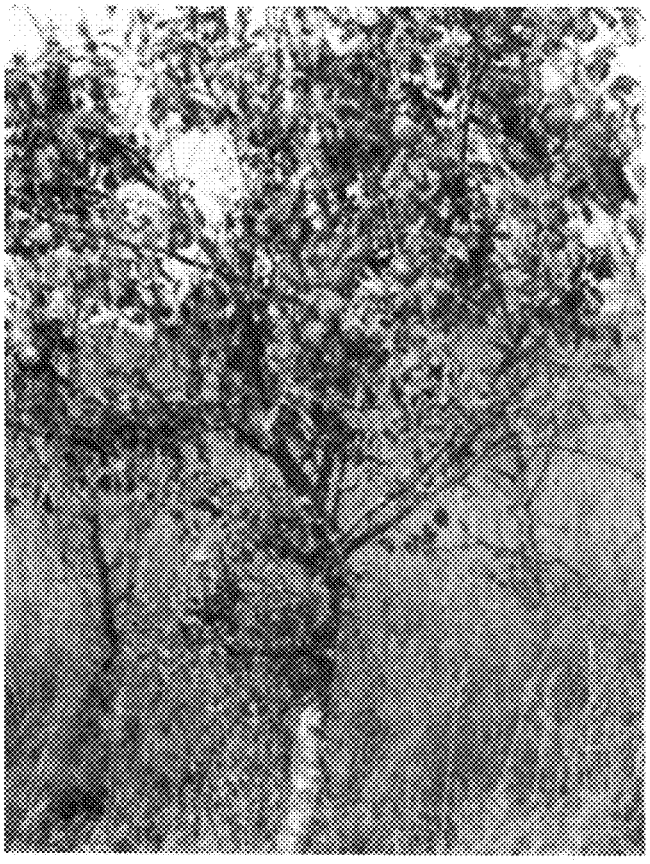
Figure 2:
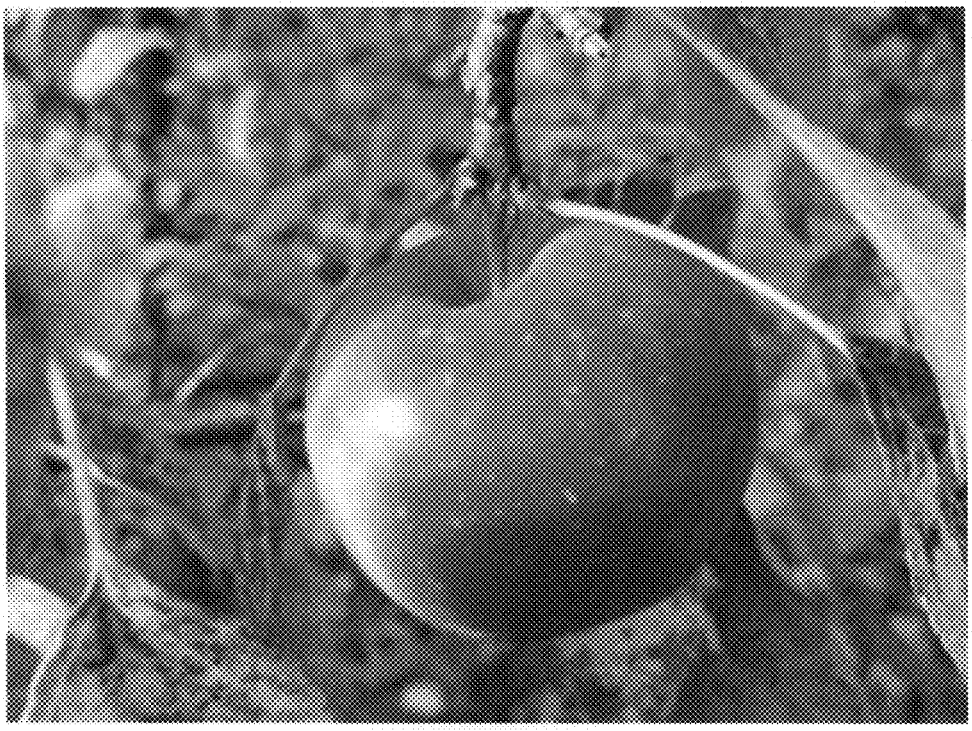

FIG. 1 shows a 'MAC 2137' apple tree;
FIG. 2 shows the fruit of a 'MAC 2137' apple tree

BACKGROUND OF THE INVENTION

'MAC 2137' is a new and distinct apple tree discovered by the inventor in 1998. The inventor saved seeds from selected apples (*Malus domestica* Mill., variety unknown) grown in a cultivated area in Fairhaven, Minn., then cultivated those seeds to produce seedlings for observation. One of those seedlings was observed to produce fruit unlike other known varieties, and was selected for further observation under the name 'MAC 2137'. In 2003 scion wood of the original 'MAC 2137' tree was budded onto 'Vineland 1' dwarfing rootstock (not patented) at Fairhaven, Minn., and second generation fruit was obtained. Further asexual propagation has been conducted, and the cultivar has been found to remain true to type through successive asexual propagations. The fruit of 'MAC 2137' is notable for its smaller size, earlier ripening, similar crunchy texture and sweeter flavor balance as compared to 'Honeycrisp' (U.S. Plant Pat. No. 7,197).

The parentage of 'MAC 2137' is unknown. The apple tree varieties most similar to 'MAC 2137' are 'Honeycrisp' and 'Minnewashta' (U.S. Plant Pat. No. 11,367). A comparison of relevant features of 'MAC 2137', 'Honeycrisp', and 'Minnewashta' is provided in Table 1 below.

TABLE 1

Comparison of 'MAC 2137' to Similar Varieties

| | MAC 2137 | Honeycrisp | Minnewashta |
|---|---|---|---|
| Fruit texture | Very crisp, juicy | Very crisp, juicy | Crisp, juicy |
| Fruit size | Small, 5.7 cm | Large, 8.5 cm | Large, 8.0 cm |
| Color of mature fruit | Intense red over-color on yellow background | Red stripe over-color on yellow background | Intense red over-color on yellow background |
| Apple scab susceptibility/ resistance | Moderately susceptible | Resistant | Susceptible |
| Harvest date | Early September | Mid to late September | Late August |

DETAILED BOTANICAL DESCRIPTION OF THE VARIETY

The following detailed botanical description is based on observations made during the 2012 growing season at Fairhaven, Minn. of six year old trees. All colors are described according to The Royal Horticultural Society Mini Colour Chart (2005). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:

*Type*.—Tall Spindle.
*Vigor*.—Strong prior to fruiting then moderate.
*Height*.—3 meters.
*Diameter*.—1.3 meters.
*Trunk diameter at 20 cm above the graft union*.—4.5 cm.

*Bark texture*.—Smooth.
*Bark color grayed brown N199C and N199A*.
*Lenticels*.—Irregular sizes, 1×2.5 mm to 3×7 mm, distribution irregular, average about 2 per $cm^2$, color — white N155A.

Branch:
*Length*.—0.6 to 1 meter.
*Diameter*.—1.5 cm.
*Crotch angle*.—15 degrees.
*Color*.—Grey-brown N199C.
*Lenticels*.—Round to elongated, 1×1 mm or 1×2 mm, grey-brown N199D, 4 per cm2.

One year old shoot:
*Length*.—0.2 to 0.6 meters.
*Color*.—Grayed purple N187A.
*Pubescence*.—Common, light to heavy, obscuring bark, underneath and toward terminal end.
*Color*.—Greyed-orange N166A.
*Thickness*.—3-4 mm at 10 cm from base.
*Internode length*.—2-3.5 cm.
*Lenticels*.—1 mm round to elongated, 7 per $cm^2$.

Winter hardiness: No injury in cold zone 4.

Leaves:
*Shape*.—Ovate.
*Apex*.—Acuminate.
*Base*.—Equilateral.
*Length*.—7.5 cm-10 cm.
*Width*.—3.5 cm-5.5 cm.
*Length/width ratio*.—1.89.
*Margin*.—Serrate.
*Upper surface*.—Smooth, green 137A.
*Lower surface*.—Slightly rough with slight pubescence, green 137C
*Venation*.—Pinnate, yellow-green 146C.
*Attitude in relation to shoot*.—Spirals around.
*Petiole*.—Length — 1.5 cm-3.5 cm.
*Diameter*.—2 mm.
*Color*.—Yellow-green 146C.
*Stipules*.—2 per petiole, length 2 mm to 5 mm, width <1 mm, pointed, margin smooth, larger stipules yellow-green 149A, smaller stipules purple 76B, violet blue 90B and others.

Flower:
*Bud (dormant)*.—Quantity per spur — 1 to 2.
*Length*.—6 mm, diameter — 3.5 mm.
*Color*.—Violet-blue 97C and greyed-orange 166A.
*Color (balloon stage) grey-brown N199D and red-purple 63B*.
*Petals*.—Quantity per flower — 5.
*Shape*.—Obelliptic to elliptic, apex acute, base aequilateral.
*Length*.—1.5 cm-2 cm.
*Width*.—1 cm-1.5 cm.
*Color of upper surface*.—White N999D with red-purple 70C towards the margins.
*Color of lower surface*.—White N999D with red 55B shading toward margin or center.
*Arrangement*.—Intermediate, touching.
*Diameter of open flower*.—3.5 cm-4 cm.
*Pedicel*.—Length — 1.2 cm-2.3 cm.
*Diameter*.—1.4 mm-2 mm.
*Color*.—Top — yellow-green 145A.
*Underneath*.—Greyed-orange 166C.
*Sepals*.—Quantity — 5.
*Color*.—Upper surface yellow-green 149D.
*Length*.—8 mm.
*Shape*.—Lanceolate with pointed tip, recurved.
*Pistils*.—Size — 0.5 cm-1 cm.
*Color*.—White 155D.
*Anthers*.—Quantity — 15-18.
*Size*.—1.5 mm.
*Pollen*.—Color — yellow 12A.
*Stigma*.—Size 1.4 cm.
*Color*.—Yellow-green 150B.
*Style*.—Size 0.5 mm-1 mm.
*Color*.—Yellow-green 150B.
*Ovary*.—Size — 4 mm.
*Color*.—Green 139C and purple N77B.
*Bloom*.—Date of first bloom — April 30th in Fairhaven, Minn.
*Date of full bloom*.—May 5th in Fairhaven, Minn.

Fruit:
*Quantity per cluster*.—1-3.
*Size*.—Height 4.7 cm, Width 5.7 cm.
*Weight*.—3 oz; Ratio of Height to Width — 0.82.
*Shape*.—Oblate.
*Ribbing*.—Insignificant.
*Depth of eye basin*.—9.5 mm.
*Width of eye basin*.—19 mm.
*Length of stalk*.—1.5 cm-2.5 cm.
*Thickness of stalk*.—1.5 mm.
*Width of stalk cavity*.—12 mm.
*Depth of stalk cavity*.—9.5 mm.
*Lenticels*.—Prominent, round, diameter 1 mm, color white 155D, density 7 per $cm^2$.
*Bloom of skin*.—Pronounced.
*Greasiness of skin*.—Some when more than three weeks past prime harvest date.
*Background color of skin*.—Yellow 8C.
*Overcolor of skin*.—Vivid red 45A.
*Amount of over color*.—70% on exposed fruit.
*Intensity of overcolor*.—Strong.
*Pattern of over color*.—Irregular blush.
*Flesh texture*.—Extremely crisp.
*Aroma*.—Mild apple.
*Juiciness*.—Juicy.
*Brix*.—14°.
*Flesh coloration*.—Yellowish white 155D; Locules — 5 per fruit, closed or slightly open, length 8 mm, width 3 mm.
*Stem coloration*.—Light greyed-brown199C.
*Fruit eating quality*.—'MAC 2137' is sweet, low acid, very crisp, juicy and aromatic. Flesh is slow to brown and stays white for several days after cutting.

Seeds:
*Seeds*.—7 to 10 per fruit, length 9 mm, width 5 mm, teardrop shape with pointed tip.
*Color brown 200A on edges, greyed-orange* 165A toward center, tip often white 155D.
*Disease resistance/susceptibility*.—Moderate susceptibility to scab and cedar apple rust.

Harvest: August 28th-September 20th in Fairhaven, Minn.
*Storage*.—'MAC 2137' is a high sugar low acid cultivar. Acid declines in storage, making flavor less appealing after early December, though crisp texture persists.

Use: Fresh Market.

I claim:

1. A new and distinct apple tree substantially as shown and described herein.

* * * * *